(12) United States Patent
Sookraj et al.

(10) Patent No.: US 10,662,139 B2
(45) Date of Patent: May 26, 2020

(54) ACRYLIC ACID PRODUCTION PROCESS (71) Applicant: Novomer, Inc., Waltham, MA (US)

(72) Inventors: Sadesh H Sookraj, Cambridge, MA (US); Alexander Tseitlin, Acton (CA); Konstantin A. Pokrovski, Spencerport, NY (US); Waheed Mukaddam, Cambridge, NY (US)

(73) Assignee: Novomer, Inc., Rochester, NY (US)

( * ) Notice: Subject to any disclaimer, the term of this patent is extended or adjusted under 35 U.S.C. 154(b) by 244 days.

(21) Appl. No.: 15/464,346

(22) Filed: Mar. 21, 2017

(65) Prior Publication Data
US 2017/0267618 A1 Sep. 21, 2017

Related U.S. Application Data (60) Provisional application No. 62/311,262, filed on Mar. 21, 2016.

(51) Int. Cl.
| | | |
|---|---|---|
| *C07C 61/09* | (2006.01) | |
| *B01J 29/08* | (2006.01) | |
| *B01J 29/40* | (2006.01) | |
| *C07C 51/44* | (2006.01) | |
| *C07C 51/50* | (2006.01) | |
| *C08F 120/06* | (2006.01) | |
| *C07C 51/09* | (2006.01) | |

(52) U.S. Cl.
CPC ............. *C07C 51/09* (2013.01); *B01J 29/084* (2013.01); *B01J 29/40* (2013.01); *C07C 51/44* (2013.01); *C07C 51/50* (2013.01); *C08F 120/06* (2013.01)

(58) Field of Classification Search
CPC ......... C07C 51/09; C07C 51/44; C07C 51/50; B01J 29/084; B01J 29/40; C08F 120/06
USPC .......................................................... 526/75
See application file for complete search history.

(56) References Cited

U.S. PATENT DOCUMENTS

| | | |
|---|---|---|
| 3,176,042 A | 3/1965 | Schnizer et al. |
| 3,647,680 A | 3/1972 | Greenwood et al. |
| 3,689,533 A | 9/1972 | Schultz |
| 3,849,457 A | 11/1974 | Haag et al. |
| 3,885,155 A | 5/1975 | Anbar |
| 4,427,884 A | 1/1984 | Anbar et al. |

(Continued)

FOREIGN PATENT DOCUMENTS

| | | |
|---|---|---|
| JP | 2013-173088 | 9/2013 |
| WO | 1994/07835 A1 | 4/1994 |

(Continued)

OTHER PUBLICATIONS

Beta Analytic Testing Laboratory, Understanding Carbon-14 Analysis, Biobased Analysis—Radiocarbon Dating or carbon 14, dated Sep. 20, 2018 https://www.betalabservices.com/biobased/barcon14-dating.html (2 pages).

(Continued)

*Primary Examiner* — Michael Bernshteyn
(74) *Attorney, Agent, or Firm* — Young Basile Hanlon & MacFarlane, P.C.

(57) ABSTRACT

Provided herein are methods of producing acrylic acid from bPL. Such methods involve the use of a heterogeneous catalyst, such as a zeolite at vapor phase conditions. The method may use a fixed bed, moving bed or fluidized contacting zone as the reactor configurations.

36 Claims, 4 Drawing Sheets

(56) References Cited

U.S. PATENT DOCUMENTS

| | | | |
|---|---|---|---|
| 4,973,841 A | 11/1990 | Purser | |
| 5,198,578 A | 3/1993 | Etzkorn et al. | |
| 5,438,194 A | 8/1995 | Koudijs et al. | |
| 5,661,299 A | 8/1997 | Purser | |
| 8,445,703 B2 | 5/2013 | Allen et al. | |
| 8,796,475 B2 | 8/2014 | Allen et al. | |
| 8,961,909 B2 | 2/2015 | Lehr et al. | |
| 9,095,510 B2 | 8/2015 | Mansouri et al. | |
| 9,096,510 B2 | 8/2015 | Porcelli et al. | |
| 9,156,803 B2 | 10/2015 | Allen et al. | |
| 9,206,144 B2 | 12/2015 | Allen et al. | |
| 9,238,210 B2 | 1/2016 | Marchant et al. | |
| 9,327,280 B2 | 5/2016 | Lee et al. | |
| 9,388,095 B2 | 7/2016 | Leroy et al. | |
| 9,403,788 B2 | 8/2016 | Lee et al. | |
| 9,493,391 B2 | 11/2016 | Allen et al. | |
| 9,567,531 B2 | 2/2017 | Fujiyama et al. | |
| 9,738,784 B2 | 8/2017 | Allen et al. | |
| 9,914,689 B2 | 3/2018 | Porcelli et al. | |
| 10,065,914 B1 | 9/2018 | Ruhl et al. | |
| 10,099,988 B2 | 10/2018 | Farmer et al. | |
| 10,099,989 B2 | 10/2018 | Sookraj | |
| 10,144,802 B2 | 12/2018 | Sookraj | |
| 10,221,150 B2 | 3/2019 | Farmer et al. | |
| 10,221,278 B2 | 3/2019 | Lee et al. | |
| 10,245,559 B2 | 4/2019 | Lapointe et al. | |
| 2008/0161624 A1 | 7/2008 | Glover et al. | |
| 2010/0113822 A1* | 5/2010 | Craciun | C07C 51/377 560/212 |
| 2011/0319849 A1* | 12/2011 | Collias | A61L 15/22 604/372 |
| 2012/0123137 A1 | 5/2012 | Allen et al. | |
| 2012/0315681 A1 | 12/2012 | Van Walsem et al. | |
| 2013/0165670 A1 | 6/2013 | Allen et al. | |
| 2013/0209775 A1 | 8/2013 | Allen et al. | |
| 2013/0281715 A1 | 10/2013 | Allen et al. | |
| 2014/0018574 A1 | 1/2014 | Raith et al. | |
| 2014/0275575 A1 | 9/2014 | Allen et al. | |
| 2014/0296522 A1 | 10/2014 | Lee et al. | |
| 2014/0309399 A1 | 10/2014 | Porcelli et al. | |
| 2015/0005513 A1 | 1/2015 | Lee et al. | |
| 2015/0141693 A1 | 5/2015 | Allen et al. | |
| 2015/0183703 A1* | 7/2015 | Wong | C07C 51/14 528/335 |
| 2015/0183708 A1 | 7/2015 | Harris et al. | |
| 2015/0299083 A1 | 10/2015 | Porcelli et al. | |
| 2015/0307437 A1 | 10/2015 | Ziemian et al. | |
| 2015/0368394 A1 | 12/2015 | Allen | |
| 2016/0016876 A1 | 1/2016 | Mahoney | |
| 2016/0102040 A1 | 4/2016 | Allen et al. | |
| 2016/0102068 A1 | 4/2016 | Allen et al. | |
| 2016/0288057 A1 | 10/2016 | Lapointe et al. | |
| 2017/0002136 A1 | 1/2017 | Sookraj | |
| 2017/0029352 A1 | 2/2017 | Sookraj et al. | |
| 2017/0073463 A1 | 3/2017 | Lee et al. | |
| 2017/0080409 A1 | 3/2017 | Farmer et al. | |
| 2017/0096407 A1 | 4/2017 | Sookraj | |
| 2017/0107103 A1 | 4/2017 | Sookraj et al. | |
| 2017/0145126 A1 | 5/2017 | Mahoney | |
| 2017/0225157 A1 | 8/2017 | Lee | |
| 2017/0247309 A1 | 8/2017 | Porcelli et al. | |
| 2018/0016219 A1 | 1/2018 | Farmer et al. | |
| 2018/0022677 A1 | 1/2018 | Sookraj | |
| 2018/0029005 A1 | 2/2018 | Sookraj | |
| 2018/0030014 A1 | 2/2018 | Sookraj et al. | |
| 2018/0030015 A1 | 2/2018 | Farmer et al. | |
| 2018/0030201 A1 | 2/2018 | Farmer et al. | |
| 2018/0057619 A1 | 3/2018 | Sookraj | |
| 2018/0094100 A1 | 4/2018 | Farmer et al. | |
| 2018/0153746 A1 | 6/2018 | Sookraj | |
| 2018/0155491 A1 | 6/2018 | Sookraj | |
| 2018/0282251 A1 | 10/2018 | Sookraj | |
| 2018/0305286 A1 | 10/2018 | Sookraj | |
| 2018/0305289 A1 | 10/2018 | Sookraj et al. | |
| 2018/0354881 A1 | 12/2018 | Farmer et al. | |
| 2018/0354882 A1 | 12/2018 | Sookraj | |
| 2019/0002385 A1 | 1/2019 | Sookraj et al. | |
| 2019/0030520 A1 | 1/2019 | Lee | |
| 2019/0031592 A1 | 1/2019 | Sookraj et al. | |
| 2019/0047972 A1 | 2/2019 | Sookraj | |
| 2019/0071538 A1 | 3/2019 | Sookraj | |
| 2019/0076834 A1 | 3/2019 | Sookraj | |
| 2019/0076835 A1 | 3/2019 | Sookraj | |
| 2019/0106532 A1 | 4/2019 | Sookraj | |

FOREIGN PATENT DOCUMENTS

| | | | |
|---|---|---|---|
| WO | 2009/155086 A2 | 12/2009 | |
| WO | 2010/118128 A1 | 10/2010 | |
| WO | 2012/030619 A1 | 3/2012 | |
| WO | 2012/051219 A2 | 4/2012 | |
| WO | WO 2012/134397 | 10/2012 | |
| WO | WO-2012134397 A1 * | 10/2012 | ............ C07C 51/14 |
| WO | 2012/158573 A1 | 11/2012 | |
| WO | WO 2013/063191 | 5/2013 | |
| WO | WO-2013063191 A1 * | 5/2013 | ............ C07C 67/36 |
| WO | 2013/122905 A1 | 8/2013 | |
| WO | 2013/126375 A1 | 8/2013 | |
| WO | WO 2013/185009 | 12/2013 | |
| WO | 2014/004858 A1 | 1/2014 | |
| WO | 2014/008232 A2 | 1/2014 | |
| WO | 2015/085295 A2 | 6/2015 | |
| WO | 2015/138975 A1 | 9/2015 | |
| WO | 2015/171372 A1 | 11/2015 | |
| WO | 2015/184289 A1 | 12/2015 | |
| WO | 2016/015019 A1 | 1/2016 | |
| WO | 2016/130947 A1 | 8/2016 | |
| WO | 2016/130977 A1 | 8/2016 | |
| WO | 2016/130988 A1 | 8/2016 | |
| WO | 2016/130993 A1 | 8/2016 | |
| WO | 2016/130998 A1 | 8/2016 | |
| WO | 2016/131001 A1 | 8/2016 | |
| WO | 2016/131003 A1 | 8/2016 | |
| WO | 2016/131004 A1 | 8/2016 | |
| WO | 2017/023777 A1 | 2/2017 | |
| WO | 2017/023820 A1 | 2/2017 | |
| WO | 2017/165323 A1 | 9/2017 | |
| WO | 2017/165344 A1 | 9/2017 | |
| WO | 2017/165345 A1 | 9/2017 | |
| WO | 2018/085251 A1 | 5/2018 | |
| WO | 2018/085254 A1 | 5/2018 | |
| WO | 2018/106824 A1 | 6/2018 | |
| WO | 2018/136638 A1 | 7/2018 | |
| WO | 2018/144998 A1 | 8/2018 | |
| WO | 2018/170006 A1 | 9/2018 | |
| WO | 2018/200466 A1 | 11/2018 | |
| WO | 2018/200471 A1 | 11/2018 | |
| WO | 2019/006366 A1 | 1/2019 | |
| WO | 2019/006377 A1 | 1/2019 | |
| WO | 2019/050649 A1 | 3/2019 | |
| WO | 2019/051184 A1 | 3/2019 | |
| WO | 2019/070981 A1 | 4/2019 | |

OTHER PUBLICATIONS

International Search Report and Written Opinion dated Jun. 7, 2017, for International Application No. PCT/US2017/023269, Applicant, Novomer, Inc. (17 pages).

International Search Report and Written Opinion dated Oct. 9, 2018, for International Application No. PCT/US2018/040397, Applicant, Novomer, Inc. (12 pages).

Fan et al., Ethylene Formation by Catalytic Dehydration of Ethanol with Industrial Considerations, Materials, Dec. 28, 2012, pp. 101-115, vol. 6, Issue 1 (15 pages).

Advisory Action received for U.S. Appl. No. 15/640,197, dated Feb. 1, 2019, 3 pages.

Final Office Action received for U.S. Appl. No. 15/640,197, dated Oct. 18, 2018, 24 pages.

International Preliminary Report on Patentability received for PCT Patent Application No. PCT/US2017/023269, dated Oct. 4, 2018, 13 pages.

(56) References Cited

OTHER PUBLICATIONS

International Preliminary Report on Patentability received for PCT Patent Application No. PCT/US2017/023302, dated Oct. 4, 2018, 7 pages.
International Search Report and Written Opinion received for PCT Patent Application No. PCT/US2017/023302, dated Jun. 5, 2017, 9 pages.
Näfe et al., "Deactivation Behavior of Alkali-Metal Zeolites in the Dehydration of Lactic Acid to Acrylic Acid", Journal of Catalysis, vol. 329, 2015, pp. 413-424.
Non-Final Office Action received for U.S. Appl. No. 15/640,197, dated Apr. 26, 2019, 38 pages.
Non-Final Office Action received for U.S. Appl. No. 15/640,197, dated May 31, 2018, 24 pages.
Non-Final Office Action received for U.S. Appl. No. 16/023,410, dated Apr. 15, 2019, 33 pages.
Yan et al., "Potassium-Ion Exchanged Zeolites for Sustainable Production of Acrylic Acid by Gas-Phase Dehydration of Lactic Acid", ACS Catalysis, vol. 7, Dec. 2, 2016, 40 pages.

\* cited by examiner

ACRYLIC ACID PRODUCTION PROCESS

CROSS REFERENCE TO RELATED APPLICATION

This application claims priority from U.S. Provisional Patent Application 62/311,262 filed Mar. 21, 2016.

FIELD OF THE INVENTION

The present invention relates to an improved process for the production of acrylic acid, and more specifically to production of acrylic acid from β-propiolactone (bPL).

BACKGROUND OF THE INVENTION

The production and use of acrylic acid (AA) has grown significantly in recent decades as the demand for polyacrylic acid-based superabsorbent polymers (SAPs) has grown. SAPs are used extensively for the manufacture of diapers, adult incontinence products, and feminine hygiene products, as well as in agricultural applications.

Currently, commercial acrylic acid is typically derived from propylene oxidation. Propylene is primarily a product of oil refining and its price and availability are closely tied to crude oil prices. Because of this, acrylic acid prices remain tied closely to the price of oil and its fluctuations.

Thus, there exists a need in the art for alternative methods to synthesize acrylic acid. At the same time, it would be preferred to produce acrylic acid from renewable resources. US patent application publications 2015/0183708 published Jul. 2, 2015 and 2014/0018574 filed Jan. 15, 2014 disclose the production of bio-based acrylic acid from poly-3-hydroxypropionate using a wide variety of biologically active materials.

Other references disclose producing acrylic acid from bPL (β-propiolactone) with inorganic catalysts. U.S. Pat. No. 3,176,042 disclosed a phosphoric acid catalyzed process for the production of acrylic acid from bPL. Due to corrosiveness of phosphoric acid and slow reaction rate this process is capital intensive. Additionally, water has to be fed to the reactor continuously to maintain the composition of phosphoric acid inside the reactor at the desired levels. This leads to the need to separate water from the produced acrylic acid resulting in additional equipment and operating costs.

U.S. Pat. No. 9,096,510 B2 teaches production of acrylic acid from bPL using a solid catalyst in at least partial gas phase conditions.

WO20133191 teaches production of acrylic acid from bPL in a two-step process: at first bPL is polymerized to produce poly-propiolactone and then acrylic acid is produced via thermolysis of poly-propiolactone. This process capital intensive and has high operating costs as highly exothermic polymerization reaction is followed by highly endothermic thermolysis reaction.

Thus, improved methods are sought to produce acrylic acid, especially high purity acrylic acid from non-hydrocarbon and preferably renewable sources.

SUMMARY OF THE INVENTION

Provided herein are methods and processes for producing acrylic acid from beta-propiolactone (bPL) via an improved one-step process for the production of acrylic acid from bPL that is economically favorable compared to processes known in the art.

In some aspects, a method and process are provided for producing acrylic acid from bPL, by combining bPL, a heterogeneous catalyst, and optionally a solvent or diluent; maintaining the bPL and any solvent or diluent in vapor phase while contacting the catalyst; and producing acrylic acid from at least a portion of the bPL. The heterogeneous catalyst comprises a crystalline microporous solid. Catalysts of the type that are specifically suited for this invention include alkaline-earth phosphates, supported phosphate salts, calcium hydroxyapatites, inorganic salts, and zeolites. In preferred embodiments, the heterogeneous catalyst is an alumina-silicate molecular sieve and more preferably a zeolite having Lewis and/or Brönsted acidity. The zeolites can be in hydrogen form or in cation exchanged form. Suitable cations are alkali metals such as $Na^+$ or $K^+$; alkali-earth cations such as $Ca^{2+}$, $Mg^{2+}$, $Sr^{2+}$, or $Ba^{2+}$; $Zn^{2+}$, $Cu^+$, and $Cu^{2+}$.

The conversion of bPL to acrylic acid can be performed in a fixed bed continuous reactor or a continuous reactor and regeneration system, i.e. a reactor and regenerator that can continuously provide fresh catalyst or regenerated catalyst to the reaction zone. Continuous regeneration reactors include moving bed and fluidized bed reactor arrangements.

In one embodiment the invention is a method producing acrylic acid that comprises passing a vapor phase feed stream comprising bPL and a polymerization inhibitor to a catalyst comprising a crystalline microporous solid at liquid or mixed phase conversion conditions; recovering a vapor phase product stream; and recovering a product stream containing acrylic acid from the fixed bed; and separating acrylic acid from the product stream in a separation zone. In another embodiment the entire conversion will take place in a single reactor.

In another embodiment the invention is a method producing acrylic acid that comprises passing a vapor phase feed stream comprising bPL to a fixed bed of a zeolite catalyst at conversion conditions; recovering a vapor phase product stream; and recovering a product stream containing acrylic acid from the fixed bed; and separating acrylic acid from the product stream in a separation zone.

Optionally, bPL can be diluted with an inert solvent or inert gas prior to be fed to the conversion reactor. Acrylic acid can be recovered from the crude reaction product in one or more distillation columns. Optionally, inert gas or solvent can be used to dilute bPL and un-reacted bPL can be recycled back to the conversion reactor.

DETAILED DESCRIPTION OF THE INVENTION

The present application can be best understood by reference to the following description taken in conjunction with the accompanying figures, in which like parts may be referred to by like numerals.

The following description sets forth methods, processes, parameters and the like to produce acrylic acid from bPL. It should be recognized, however, that such description is not intended as a limitation on the scope of the present invention but is instead provided as a description of exemplary embodiments.

Provided herein are methods of producing acrylic acid from bPL using heterogeneous catalysts. Suitable heterogeneous catalysts comprise silica-alumina molecular sieves, particularly those modified with phosphate compounds. Catalysts of the type that are specifically suited for this invention include alkaline-earth phosphates, supported phosphate salts, calcium hydroxyapatites, inorganic salts, metal oxides, and zeolites. In preferred embodiments, the heterogeneous catalyst is an alumina-silicate molecular sieve and more preferably a zeolite having Lewis and/or Brönsted acidity. The zeolites can be in hydrogen form or in cation exchanged form. Suitable cations are alkali metals such as $Na^+$ or $K^+$; alkali-earth cations such as $Ca^{2+}$, $Mg^{2+}$, $Sr^{2+}$, or $Ba^{2+}$; $Zn^{2+}$, $Cu^+$, and $Cu^{2+}$. Such methods produce acrylic acid from bPL in a single step reaction. Such methods may also produce acrylic acid in high yields, by minimizing other by-products that may form, such as poly-propiolactone and polyacrylic acid.

There are multiple process configurations for the reaction zone of this invention. The reaction zones will preferably be continuous with respect to the feed flow and will utilize a fixed bed, moving bed or fluidized particle reactor. The reactors will operate in the vapor phase. The fixed bed reactor arrangement may operate under atmospheric, sub-atmospheric (under vacuum), or super-atmospheric pressure and bPL enters the reactor in vapor phase. The bPL may enter the reactor in a diluted or undiluted state. The moving bed form of the continuous regeneration reactor may operate in the same manner. In the case of the fluidized particle form of the continuous regeneration reactor the bPL may enter the reaction zone together with inert gas (such as nitrogen) that together provide the suspended/fluidized in the flow the catalyst in the gas. Optionally, the bPL can be diluted in a solvent in any of the above described process arrangements.

The various reactor arrangement can operate under a variety of conditions. The conversion of bPL to acrylic acid may be conducted in the temperature range from 100° C. to 300° C., preferably from 150° C. to 250° C., and more preferably from 150° C. to 225° C. Suitable pressure conditions range from vacuum conditions to pressures up to 100 psig.

The product stream of the reaction contains acrylic acid and other materials attendant to the operation of the process. Such other materials may include low-boiling by-products (such as ethylene and $CO_2$), optionally inert gas (such as nitrogen), unreacted bPL and di-acrylic acid (dimer of acrylic acid), additional by products and diluents. The acrylic acid is recovered from the reaction products by means known in the art such as distillation in one or more distillation columns. It is well known in the art that when condensed at elevated temperatures (at temperatures greater than 80° C.) acrylic acid tend to form di-acrylic acid and polyacrylic acid. Thus, the formed acrylic acid needs to be rapidly cooled as soon as it exits the reactor.

In some embodiments, the bPL used in the methods described herein may be produced by epoxide carbonylation. For example, the bPL may be produced from ethylene oxide and carbon monoxide via a carbonylation reaction. See e.g., WO2010/118128. In one variation, the bPL is produced by reacting ethylene oxide with carbon monoxide in the presence of a carbonylation catalyst and optionally a solvent.

In some variations, the bPL is added to the reaction with an initial pressure of carbon monoxide. In other variations where the method is continuous, no initial pressure is required to add the bPL.

In some embodiments a polymerization inhibitor is used in the conversion of the bPL to acrylic acid. The polymerization inhibitor may be a radical polymerization inhibitor. Suitable polymerization inhibitors may include, for example, phenothiazine. In other embodiments radical polymerization inhibitor is added at acrylic acid product recovery step after the vapor phase conversion reactor.

In some embodiments of the methods described herein, the conversion of bPL to acrylic acid is performed neat. In other embodiments, the conversion of bPL to acrylic acid is performed in the presence of a solvent or diluent.

In some variations, the solvent selected (i) dissolves, or at least partially dissolves, the bPL, but does not react, or minimally reacts, with the bPL; or (ii) has a high boiling point so that the acrylic acid produced may be distilled while solvent remains in the reactor, or a combination of (i) and (ii). In certain variations, the solvent is a polar aprotic solvent. For example, the solvent may be a high boiling polar aprotic solvent. In one variation, the solvent includes sulfolane.

The amount of solvent used may be varied to balance the metering of bPL added and the overall concentration of reagents in the reaction mixture. For example, in one variation, the ratio of bPL to solvent in the reaction is from about 3:1 to about 1:5.

The solvent may be dried using any suitable methods or techniques known in the art prior to use.

A combination of any of the solvents described herein may also be used.

A number of variable can affect the process, for example, the rate of bPL addition may affect the yield of acrylic acid. In some variations, the method further includes controlling the rate of addition of bPL. A slower rate of bPL addition was also unexpectedly observed to reduce the formation of other products, such as poly-propiolactone and polyacrylic acid. In some variations, the method further includes minimizing or suppressing production of poly-propiolactone from at least a portion of the bPL. In one variation, little or no poly-propiolactone is produced. In other variations that may be combined with the foregoing, the method further includes minimizing or suppressing production of poly-acrylic acid from at least a portion of the acrylic acid produced. In one variation, little or no polyacrylic acid is produced.

The amount of bPL added may be metered by any suitable methods or techniques in the art. Such addition methods will vary with the scale of production to which the method is employed. Such addition methods may range from adding bPL in lab scale quantities by metering into the reactor via a needle valve to large scale addition through one or more valve and manifold arrangements. For fixed and moving bed operations the contacting may be at a throughput in a range of relative weight hourly space velocity (WHSV) of bPL between 0.1 $h^{-1}$ to 2.1 $h^{-1}$ or between 0.3 $h^{-1}$ and 0.9 $h^{-1}$.

The removal of acrylic acid produced may also affect the yield of acrylic acid. Stripping off of the acrylic acid produced was also unexpectedly observed to increase yield of the acrylic acid produced. In some variations, the method further includes stripping off at least a portion of the acrylic acid produced (e.g., by distillation). In certain variations of the foregoing, stripping off at least a portion of the acrylic acid produced minimizes polymerization of the acrylic acid, and thus, formation of polyacrylic acid.

In some embodiments, the acrylic acid may be produced at a pressure that strips off at least a portion of the acrylic acid produced. For example, in one variation, the method may be performed at subatmospheric pressure of 100 mm Hg (absolute). In other variations, reaction can be conducted at the absolute pressure between 20 mm Hg and 200 mm Hg. Yet in another variation bPL is converted to acrylic acid at superatmospheric pressure in the range of 0.5-100 psig.

The acrylic acid may be produced at elevated temperatures according to the methods described herein. In some embodiments, the temperature is at least 100° C., at least 150° C., at least 200° C., at least 250° C. or at least 300° C. and may be in a range of between 100° C. to 300° C., between 150° C. and 250° C., and or between 190° C. and 240° C.

In some variations, the reactor in which the method is performed, the bPL, polymerization inhibitor, catalyst, and/or solvent is heated to the temperatures described herein in the reaction zone. In other variations, the bPL, polymerization inhibitor, catalyst, and/or solvent is provided to the reactor at the temperatures described herein.

In some embodiments of the methods described herein, acrylic acid is produced at a yield of at least 50%, at least 55%, at least 60%, at least 65%, at least 70%, at least 75%, at least 80%, at least 85%, at least 90%, or at least 95%.

In some embodiments of the methods described herein, the acrylic acid produced has a purity of at least 95%, at least 96%, at least 97%, or at least 98%. In some variations where the acrylic acid produced is isolated, e.g., by distillation, the acrylic acid has a purity of at least 98%, at least 98.5%, at least 99%, at least 99.1%, at least 99.2%, at least 99.3%, at least 99.4%, at least 99.5%, at least 99.6%, at least 99.7%, at least 99.8%, or at least 99.9%.

The deactivation of the catalyst will occur over time as a result of at least one of organic material depositing on the surface of the catalyst and the production of coke within the pores and on the surface of the zeolite and/or the accumulation of polar, acidic compounds. The composition of the catalyst along with operating conditions, primarily temperature will determine the rate of catalyst deactivation by coke formation. Removal of coke and organic material by combustion at elevated temperatures can effectively restore the activity of the catalyst. Regeneration will typically occur at a temperature of 450° C. or higher. Preferably regeneration will be in a range of between 450° C. and 550° C.

For fixed bed reactors an in situ calcination of the deactivated catalyst can effect regeneration and restore its activity. Typically, calcination will pass an oxygen containing regeneration gas, in most cases air, through the catalyst bed at temperature 450° C. or more. Regeneration will typically occur at a temperature of 450° C. or higher. Preferably regeneration will be in a range of between 450° C. and 550° C. and for a period of from 4 to 10 hours. Gas flow may be continued for a selected time period to remove at least a portion of the deactivation deposits from the catalyst or until an essentially complete removal of the coke and any organic material takes place as evidence by the lack of combustion product in the spent gas (flue gas) from the regeneration step. In other embodiments the regeneration of the fixed or moving bed catalyst will include purging the regenerated catalyst with a an inert gas stream at a temperature of below 400° C. and more preferably the inert gas stream will comprise nitrogen.

The heterogeneous catalyst comprising the crystalline microporous solids include alkaline-earth phosphates, supported phosphate salts, calcium hydroxyapatites, inorganic salts, and zeolites. In preferred embodiments, the heterogeneous catalyst is molecular sieve and more preferably an alumina-silicate molecular sieve. In most embodiments the heterogeneous catalyst will have Lewis and/or Brönsted acidity and more preferably is a zeolite with Lewis acidity. In other embodiments such molecular sieves may be beneficially modified with phosphate compounds. Catalysts of the type that are specifically suited for this invention include alkaline-earth phosphates, supported phosphate salts, calcium hydroxyapatites, inorganic salts, and zeolites. In preferred embodiments, the heterogeneous catalyst is an alumina-silicate molecular sieve and more preferably a zeolite having Lewis and/or Brönsted acidity. The zeolites can be in hydrogen form or in cation exchanged form. Suitable cations are alkali metal cations such as $Na^+$ or $K^+$; alkali-earth cations such as $Ca^{2+}$, $Mg^{2+}$, $Sr^{2+}$, or $Ba^{2+}$; $Zn^{2+}$, $Cu^+$, and $Cu^{2+}$.

With respect to the preferred zeolite catalysts, a broad range of zeolites and zeolite framework types may be beneficially used to practice this invention. The different zeolite framework types that may be most beneficially used in this invention comprise MFI (pentasil), FAU (faujasite), MAU (mordenite), BEA (beta) and MWW zeolite structures. Useful zeolites from these classes may comprise one-dimensional (1D: ZSM-22), two-dimensional (2D: MCM-22 and ZSM-35), or three dimensional (3D: ZSM-5, ZSM-11, ZSM-5/ZSM-11, and β) crystalline configurations. In one embodiment preferred zeolites include ZSM-5, zeolite beta, zeolite Y, and zeolite A.

While not wishing to be bound by any theory, a higher silica alumina ratio in the zeolite would mean a lower population of framework Al and thus a lower capacity for exchangeable charge-compensating alkali ions (K++Na+). Such locations serve as Lewis acidic sites. Thus, it is believed that the surface acidity decreases with increasing silica alumina ratio for most of the zeolite catalysts. Accordingly, in one embodiment the solid catalyst possesses both weakly acidic and weakly basic sites. In a further embodiment the solid catalyst has a balance between the surface acidity and basicity. In another embodiment preferred zeolites will have a SiO2/Al2O3 ratio in a range of between 1.1 to 120; 10 to 50; or 10 to 20.

Preferably the zeolites are ion exchanged with one or more alkali metal cations such as $Na^+$ or $K^+$; alkali-earth cations such as $Ca^{2+}$, $Mg^{2+}$, $Sr^{2+}$, or $Ba^{2+}$; $Zn^{2+}$, $Cu^+$, and $Cu^{2+}$. Of this group the zeolites are preferably ion exchanged with potassium cations. Particularly preferred zeolites are potassium exchanged ZSM-5, BEA zeolites Zeolite A and Zeolite Y. In another embodiment the zeolite is a Zeolite Y modified with alkali or alkaline-earth metals that contains both mild acid and basic sites. In some preferred embodiments the fractional exchange degree of K+ is higher than 70%, higher than 80% or higher than 90%.

In some embodiments of the zeolite has a micropore volume of at least 30%. In one preferred embodiment the zeolite has a micropore volume in the range of between 30-80% or 60 to 80%. In another preferred embodiment the zeolite is a ZSM-5 zeolite or a Y zeolite having a micropore volume in a range of from 30 to 45%.

In another embodiment the catalyst is preferably a sodium form ZSM-5 or beta zeolite that an at least 50%, at least 70% or at least 90% exchange of potassium cations with the available cation exchange sites. In another embodiment the catalyst is preferably a sodium form ZSM-5 that has an at least 50%, at least 70% or at least 90% exchange of potassium cations with the available cation exchange sites and a SiO2/Al2O3 ratio in a range of between 20 and 120, of between 20 and 50 or between 20 and 30.

In some embodiments the particle sizes were in the range of between 0.1-1.8 µm and preferably 0.2-1.8 µm.

In certain embodiments the invention will produce high yields at good selectivity. The invention may attain selectivities to AA of greater than 50%, 60%, or 80%. The yield of AA may be greater than 50%, 60%, or 75%.

Zeolites having a one dimensional 10-ring zeolite (ZSM-22) may be especially suited for use in the continuous regeneration reactor arrangements. The larger lattice space provided by such zeolites may be better suited for this unimolecular reaction and provide improvements in selectivity and/or conversion of the bPL to AA. However, the reduced number of pores per volume of zeolite associated with the larger lattice space can lead to faster filling of the pore volume of carbon deposits and organic materials. While not wishing to be bound by any theory it is believed that when acid sites particularly Lewis acid sites reside mostly in the micropores the zeolite, such pores are readily deactivated through pore blockage with coke or other material, but the greater unit volume of such micropores may slow the overall deactivation of the zeolite. In contrast dealuminated and base-treated zeolites containing a secondary mesoporous network provide greater size pores, but an overall reduced pore volume. Thus, the greater occurrence of larger ring openings of such structures may improve the production of AA, at the expense of greater susceptibility to and faster rates of deactivation due to the reduction of overall pore volume. Continuous regeneration reactor arrangements allow the method to gain the benefits in AA production from bPL while avoiding the need to take the reactor off-line for frequent regeneration of the zeolite catalyst.

Conversely when practicing the method in a fixed bed arrangement it may be advantageous to use zeolites that provide a two or three dimensional pore structure. By use of such crystalline structures any reduction in selectivity or conversion can be balanced against longer life of the zeolite catalyst in the fixed bed. In this regard zeolites with the pentasil structure, namely ZSM-11 and ZSM-5 are preferred since they may produce the least amounts of carbon deposits.

A combination of any of the catalysts described herein may also be used.

The method of the invention may be practiced in a wide variety of arrangements. The following description of specific process arrangements is not intended to limit the invention to any of any of the specific configuration of the process arrangement described herein.

In one possible arrangement of the reactor system of the invention, the reactor system is a continuous fixed bed reactor. In another possible arrangement of this invention the reactor system comprises a moving bed reactor with optional continuous catalyst regeneration. In either of these embodiments the reactor may operate at subatmospheric or superatmospheric pressure. Specifically, the reactor is preferably operated at the absolute pressure between 40 mmHg and 250 mmHG or from 0.5 psig to 100 psig. bPL is vaporized at the temperature between 80° C. and 150° C. and then bPL vapors are fed to the inlet of the reactor packed with catalyst.

The reactor is operated in the temperature range from 100° C. to 300° C., and preferably from 150° C. to 250° C. To facilitate temperature control and removal of the heat produced during the reaction the reactor can be a tubular shell-and-tube reactor with the catalyst loaded into the tubes and heat transfer fluid is fed to the shell side. Optionally, the reactor may consist of several sections and additional heat exchangers installed between sections. In one embodiment all bPL is converted inside the reactor with the selectivity to acrylic acid greater than 50% that 90% and preferably greater than 95% and most preferably greater than 99%. In another embodiment only part of bPL is converted to acrylic acid and another part of bPL is exiting the reactor unconverted. Unconverted bPL can be recovered recycled back to the inlet of the reactor. The bPL to AA conversion in this embodiment is greater than 50%, greater than 70%, greater than 80%, greater than 90% or greater than 95%. The residence time in the reactor is sufficient to achieve the desired bPL conversion and is in the range from 0.1 second to 2 minutes.

Optionally, if catalyst activity decreases, it can be regenerated in a flow of air or dilute oxygen to remove deposited coke. Such regeneration may be carried on a batch basis wherein flow of input streams to the reactor are suspended while the regeneration gas and other rejuvenating gases are passed through the catalyst in the reactor vessel. Regeneration will typically comprise an oxygen containing gas that will oxidize the coke and other volatile compounds present on the catalyst and that are causing or contributing to the deactivation of the catalyst. The regeneration gas may be heated to initiate combustion of the deactivating compounds. The heating of the combustion gas is typically only needed as regeneration is initiated and the heat released by the exothermic reaction of the coke and volatile compound with the regeneration gas will provide ample heat and in most gases excess heat in the reaction zone. For this reason the concentration of oxygen or other oxidizing reactant in the regeneration is usually fed to the deactivated catalyst in dilute phase as the regeneration is initiated or continues.

Regeneration gas continues to pass to the reactor until the desired amount of carbonaceous and volatile compounds are removed from the catalyst. In most cases regeneration continues until it is essentially complete as shown by the removal of all carbonaceous deposits and volatile compounds from the catalyst. In most cases the addition of the oxidizing gas will initiate a burn wave that starts where the regeneration catalyst first contacts the bed of catalyst and progresses through the bed in the direction of gas flow until the catalyst bed is completely regenerated.

Once the regeneration is complete, additional gases may be passed through the bed. Inert gases may be passed through the bed to cool the catalyst. Other gas stream may pass through the catalyst bed to condition the catalyst and may include such steps as impregnation and ion exchange of the catalyst.

Following any further conditioning the reactor may be brought back on-line for production of AA. This may begin by purging of the void space of the reaction zone of any residual gases followed by of the addition of vapor phase bPL into the reactor.

Other methods of regeneration may be employed and include those previously described herein. Specifically, the reactor may be operated as moving bed wherein the catalyst moves slowly, typically intermittently, through the bed under gravity flow as catalyst is withdrawn from the bottom of the reaction zone for regeneration. Such systems are shown in U.S. Pat. No. 3,647,680, the teachings of which are hereby incorporated by reference. In one embodiment of such an operation the deactivated catalyst particles descend downward through the reactor on an intermittent basis as catalyst for regeneration is removed from the bottom of the reactor and lifted to the top of a regeneration zone for passage thereto.

The regeneration zone typically performs the same steps as previously described for the in-situ regeneration of the catalyst in the fixed bed reaction zone. The regeneration may provide such steps in a batch flow manner of as catalyst particles descend intermittently through the reaction zone and various stages of regeneration and treatment. The moving bed reaction zone may operate at sub-atmospheric, atmospheric or under pressure. The catalyst may be transferred between the reactor and the regeneration zone in a manner that maintains essentially the same pressure condition in each zone or the reaction zone and the regeneration zone may operate at different pressures including operation with vacuum conditions in the reaction zone. The invention may employ one or pressure isolation chambers, often referred to as lock hoppers, between the reactor and regeneration zones to vary the pressure relative pressure between the zones.

In another possible reactor system arrangements the reactor system is again a continuous fixed bed reactor or a moving bed reactor with continuous catalyst regeneration. In this case the reactor system may be operated at atmospheric pressure, at the pressure below atmospheric pressure, or at the pressure above atmospheric pressure. In one embodiment, the reactor is operated the pressure between 250 mmHg and 50 psig. Preferably the reactor is operated at the pressure from 5 psig to 30 psig. The reactor may operated in a temperature range between 100° C. and 300° C., and preferably between 150° C. and 250° C. bPL is fed to the reactor in the flow of nitrogen or another inert gas. The weight ratio of bPL to inert gas is from 0.05:1 to about 1.5:1. In one embodiment, inert gas is fed to the vessel containing liquid bPL that is maintained at the temperature required to achieve the desired concentration of bPL in the inert gas. Then the mixture of bPL and inert gas is fed to the inlet of the reactor. In another embodiment bPL is injected into the stream of inert gas near the inlet of the reactor. In yet another embodiment, bPL is fed as solution in inert solvent. The concentration of bPL solution be in a range between 10% and 99%.

To facilitate temperature control and removal of the heat produced during the reaction the reactor can be a tubular shell-and-tube reactor with the catalyst loaded into the tubes and heat transfer fluid is fed to the shell side. Optionally, the reactor may consist of several sections and additional heat exchangers installed between sections. In one embodiment all bPL is converted inside the reactor with the selectivity to acrylic acid greater that 90% and preferably greater than 95% and most preferably greater than 99%. In another embodiment only part of bPL is converted to acrylic acid and another part of bPL is exiting the reactor unconverted. Unconverted bPL can be recovered recycled back to the inlet of the reactor. The bPL conversion in this embodiment is greater than 75%, preferably, greater than 90%, and most preferably greater than 95%. The residence time in the reactor is sufficient to achieve the desired bPL conversion and is in the range from 0.1 second to 2 minutes.

The inert gas is separated from the reaction products and is recycled back to the reactor. Optionally, if catalyst activity decreases, it can be regenerated in a flow of air or dilute oxygen to remove deposited coke.

Alternatively catalyst deactivation can again be addressed by operating the subject reactor arrangement in moving bed mode as previously described herein.

The method of this invention may also operate with a fluidized reaction zone and regeneration zone that maintains the catalyst in fluidized transport mode. This arrangement is preferred for the use of catalysts the experience rapid deactivation by the accumulation of coke and other organic or inorganic compounds on the surface or in the pores of the catalyst. Preferably the reactor is equipped with a regeneration zone: the deactivated catalyst is carried from the reaction zone to the regeneration zone and then regenerated catalyst is fed back to the reaction zone. Processes that use solid catalyst particles in a fluidized state for the cyclic contacting of the catalyst with reactants and regeneration gas are well known. (See U.S. Pat. Nos. 9,567,531; 9,388,095 and 9,238,210 the contents of which are hereby incorporated by reference.)

The reactor may also be operated below atmospheric pressure, at atmospheric pressure or above atmospheric pressure. In one embodiment, the reactor is operated the pressure between 40 mmHg and 100 psig. Preferably the reactor is operated at the pressure from 5 psig to 50 psig. The reactor is operated in the temperature range from 100° C. to 300° C., and preferably from 150° C. to 250° C.

In one embodiment the reaction section of the fluidized reaction zone comprises a fluidized bed of solid catalyst particles wherein the passage of fluidizing gas does not transport the appreciable amounts of the catalyst out of the fluidized bed and the bPL feed stream passes into the fluidized bed. The density of the catalyst in the fluidized bed will typically be at least 25 lbs per cubic foot and more typically the catalyst will have a density in a range between 30 to 35 lbs per cubic foot. In another embodiment all or a portion of the bPL feed stream may provide a portion of the gas needed to maintain fluidization of the fluidized particles in the fluidized bed. In another embodiment additional gases are added to maintain fluidization of the catalyst particles in the fluidized bed.

In another embodiment the reaction section of the fluidized reaction zone comprises a transport reaction zone wherein the catalyst particles are entrained in and carried by a fluidization gas as contacting takes place between the vapor phase feed stream and the catalyst particles. In the case of a transport reaction zone the vapor phase stream provides at least a portion of the fluidization gas. The catalyst density in the transport reaction zone will typically be less than 20 lbs per cubic foot and more typically in a range of from 5 to 15 lbs per cubic foot.

When continuous regeneration is also provided, regeneration gas will provide at least a portion of the fluidizing gas for fluidized movement of the catalyst within and from the regeneration zone. Inert gas such as nitrogen may also be fed to the reaction zone and/or the regeneration zone as additional fluidization media to further assist with the transport of the catalyst between the reaction and regeneration zones.

The temperature of the gas stream entering the reactor can be adjusted to maintain the reactor at the desired temperature. In preferred embodiment bPL is injected into the bottom of the reactor and the reaction product (acrylic acid), by-products, and inert gas are exiting from the top of the reactor. The inert gas is separated from the reaction products and recycled to the inlet of the reactor.

In another embodiment catalyst particles are removed from the vapor phase product stream as part of its recovery from the fluidized bed reaction zone ore the transport reaction zone. In some embodiments of the fluidized bed arrangement, cyclones or other gas separation apparatus will remove catalyst particles and especially catalyst fines that become entrained with the gas streams that flow out of the reaction zone or the regeneration zone. (Catalyst fines comprise broken catalyst particles along with small catalyst particles and catalyst residue created by abrasion of catalyst particles as they contact each other and surfaces of the process equipment in their fluidized state.)

In one embodiment all bPL is converted inside the reactor with the selectivity to acrylic acid greater that 90% and preferably greater than 95% and most preferably greater than 99%. In another embodiment only part of bPL is converted to acrylic acid and another part of bPL is exiting the reactor unconverted. Unconverted bPL can be recovered recycled back to the inlet of the reactor. The bPL conversion in this embodiment is greater than 75%, preferably, greater than 90%, and most preferably greater than 95%. The residence time in the reactor is sufficient to achieve the desired bPL conversion and is in the range from 0.1 second to 2 minutes.

The inert gas is separated from the reaction products and is recycled back to the reactor.

The reaction products exiting the reactor consisting of acrylic acid, optionally unreacted bPL, optionally solvent, and optionally inert gas are rapidly cooled and then acrylic acid is separated from the reaction products in one or more distillation columns.

Figure 1:
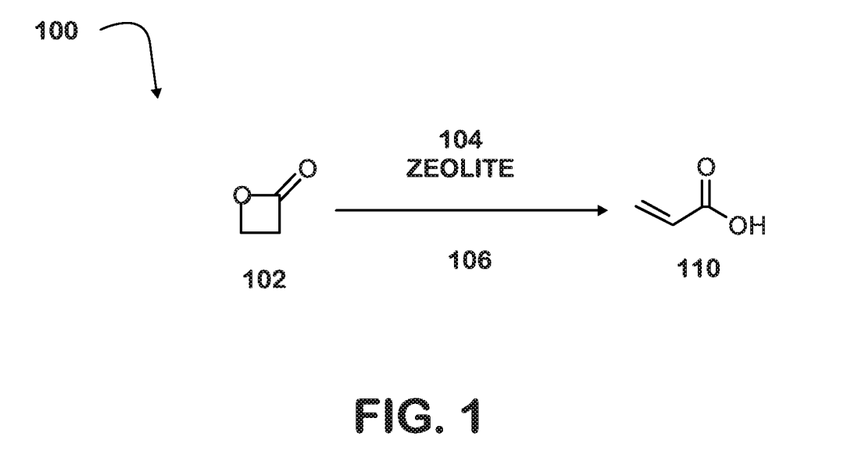
FIG. 1 depicts an exemplary process to produce acrylic acid from bPL in the presence of a zeolite and a polymerization inhibitor.

In some aspects, provided is a method of producing acrylic acid from beta-propiolactone, by combining beta-propiolactone, a zeolite, and optionally a polymerization inhibitor; and producing acrylic acid from at least a portion of the beta-propiolactone. For example, with reference to FIG. 1, process 100 is an exemplary process to produce acrylic acid. Beta-propiolactone 102 is combined with zeolite 104 and polymerization inhibitor 106 to produce acrylic acid 110. In some variations, process 100 is performed neat. In other variations, process 100 is performed in the presence of a solvent. In some embodiments, the method further includes continuously isolating the acrylic acid produced. In some variations, the acrylic acid is isolated by distillation. In other aspects, provided herein are systems for production of acrylic acid. For example, with reference to FIG. 2, an exemplary acrylic acid production system is depicted. System 200 is configured to produce acrylic acid from bPL, according to the methods described herein.

Figure 2:
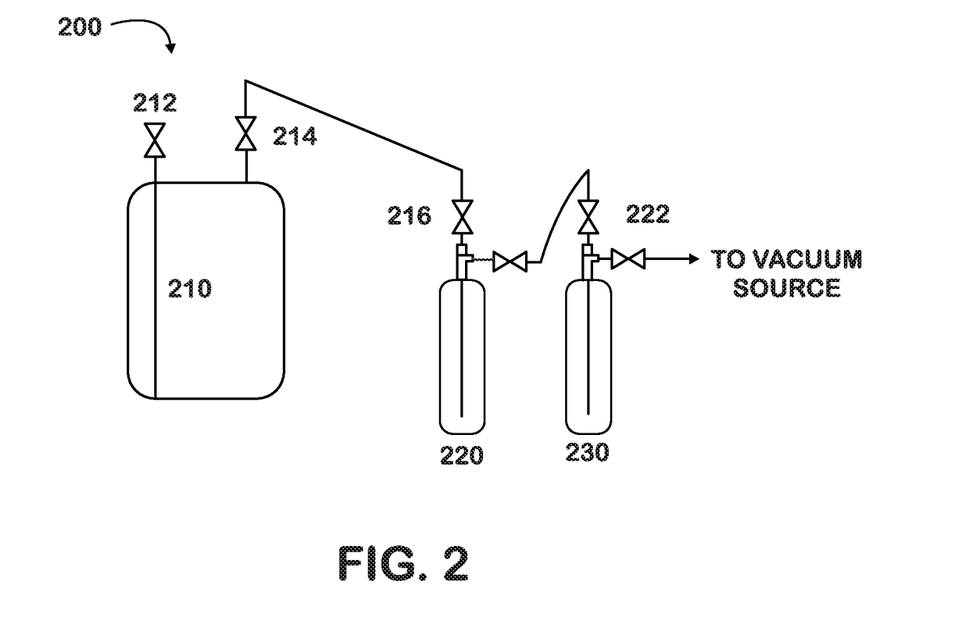
FIG. 2 depicts an exemplary reaction system to produce acrylic acid from bPL according to the methods described herein.

System 200 includes reactor 210, configured to receive bPL, a zeolite, and a polymerization inhibitor, and to produce acrylic acid from at least a portion of the bPL according to the methods described herein. Reactor 210 is configured to produce acrylic acid at an elevated temperature. Any of the temperatures described herein for the methods may be employed in the system. For example, in one variation, reactor 210 is configured to produce acrylic acid at a temperature between 170° C. and 200° C. Suitable reactors may include, for example, a Parr reactor.

In some variations, reactor 210 is configured to control the rate of addition of one or more of the bPL, the zeolite, and the polymerization inhibitor added. For example, in one variation, a mixture of the bPL and the polymerization inhibitor may be slowly added using a control valve to a mixture of catalyst in a solvent.

With reference again to FIG. 2, reactor 210 further includes vapor port 214. In some variations, reactor 210 is configured to continuously strip off at least a portion of the acrylic acid produced, and vapor port 214 is configured to pass acrylic acid vapors to collection vessel 220.

With reference again to FIG. 2, system 200 further includes acid/base scrubber 230, configured to receive acrylic acid from collection vessel 220. In other variations of the system, acid/base scrubber 230 may be omitted. Further, with reference to FIG. 2, elements 212, 216 and 222 are dip tubes.

Figure 3:
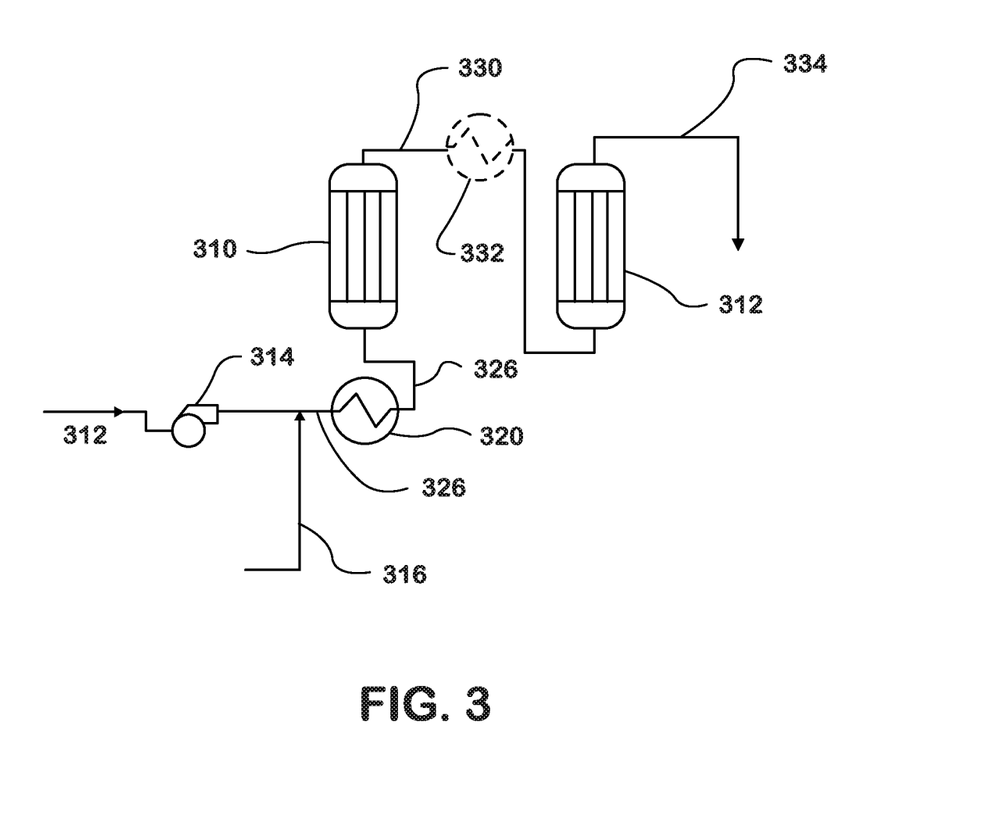
FIG. 3 is a process flow diagram for a fixed bed operation of the reactor system to produce acrylic acid from bPL according to the methods of this invention.

FIG. 3 presents the method of this invention in an arrangement suitable for commercial practice of the invention in a fixed bed configuration. A bPL feed that may optionally be admixed with a solvent enters the process via a line 312. A pair of reactors 310 and 312 each retaining multiple tubular beds of catalyst are configured to receive bPL from the feed line 312 at rate controlled by a feed pump 314 to control the rate of addition of bPL. The tubular form of reactor is preferred for removing heat from the catalyst bed during the reaction, but is not required and other types of reactors and arrangements may be used. In particular, the depiction of two reactors is for illustration purposes only and the process may use a single reactor or any number of reactors. Input line 316 may optionally supply additional process input streams such as diluents into admixture with the contents of line 324 to produce a reactor input stream 326.

Reactor input stream 326 undergoes heating to produce a vapor phase feed stream. A heat exchanger 320 supplies a heat input to reactor input stream 326. Heat may be from an internal process stream or from an external heat source. The heating will be sufficient to insure that the reactor input stream is in a complete vapor phase before it enters reactor 326.

The contents of the feed stream are converted at least in part to acrylic acid in reactor 310 and reactor 312. A transfer line 330 passes an intermediate stream containing unconverted bPL and acrylic acid along with any additional input materials added with the bPL to reactor 312. An optional heat exchanger 332 may be added to control and adjust, typically by heat removal, the temperature of the intermediate stream before it enters reactor 312. An effluent stream 334 is recovered from reactor 312. Reactor effluent stream 334 contains any unconverted bPL, acrylic acid and any additional input materials that may have been added to the reactor input stream 326.

Typically a product separation section (not shown) receives effluent stream 334 to recover the acrylic acid product. Along with recovery of the acrylic acid product the separation section will in most cases also recover unconverted bPL (which is usually recycle) and the diluent and the other additive streams that may have been added with the feed and are still recoverable while also rejecting unwanted by-products.

Figure 4:
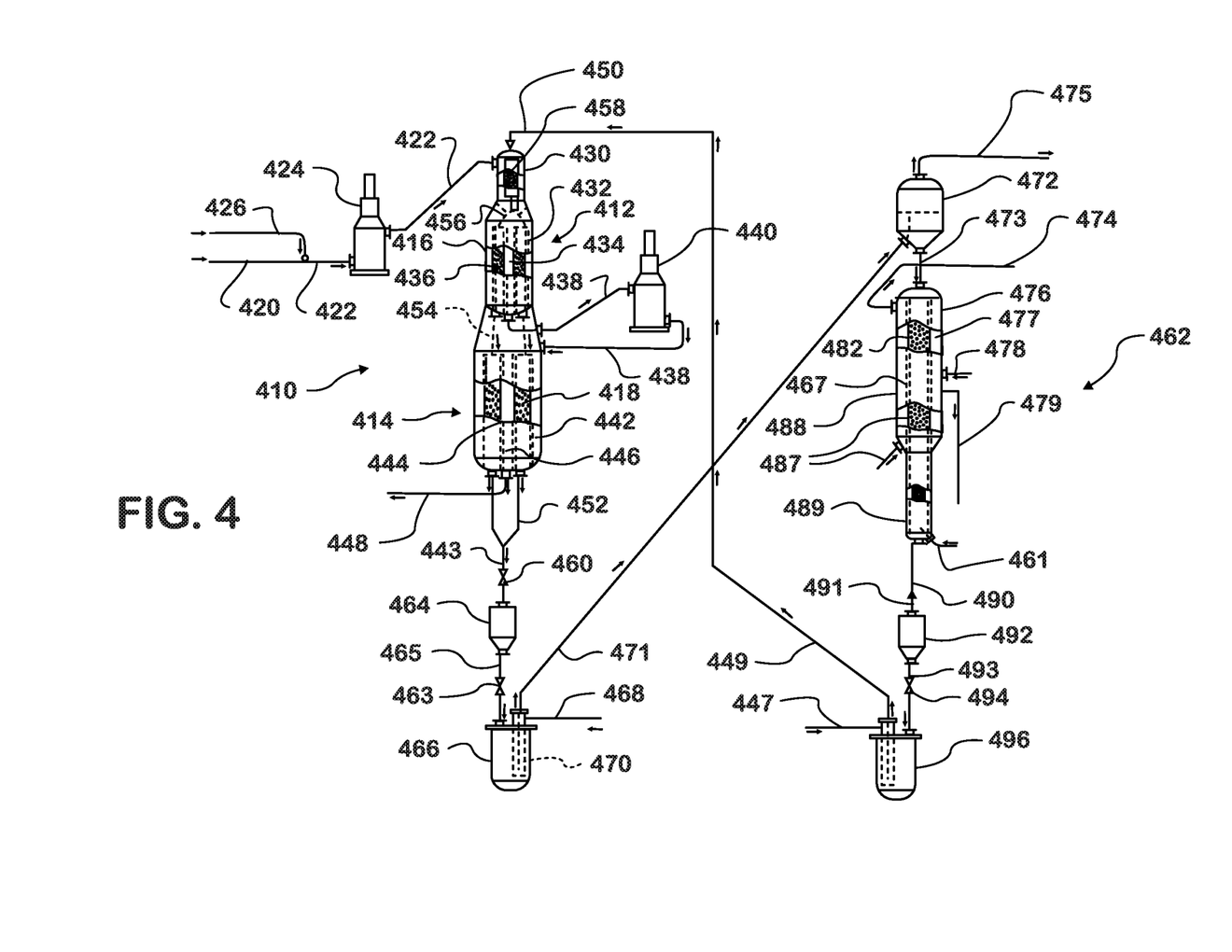
FIG. 4 is a process flow diagram for a moving bed operation of the reactor system to produce acrylic acid from bPL according to the methods of this invention.

FIG. 4 presents the method of this invention in an arrangement suitable for commercial practice of the invention in a moving bed configuration. A reactor vessel 410 houses an upper reaction section 412 that holds a bed of catalyst 416 and a lower reaction section 414 that holds a bed of catalyst 418, with both reactor beds arranged for radial flow of reactants across each reactions section.

With respect to fluid flow reactor vessel 410 is configured to receive a combined bPL feed stream comprising bPL. A feed line 420 delivers a bPL feed and an additive line 426 delivers any additives for combination into a combined feed 422 that passes through a heater 424 that heats the combined feed to insure delivery of an all vapor phase combined feed stream to reactor section 412. The combined feed passes through a heat exchange vessel 430 that is provided in some embodiments to heat catalyst that is entering reactor vessel 410 via a catalyst transfer line 450. The combined feed flows downward into an annular distribution space 432 that distributes it around catalyst bed 416. After the combined feed passes through bed 416 a center pipe 436 collects an upper reactor effluent comprising AA, unreacted combined feed and any remaining additives for transfer from the vessel into an inter-heater 440 via a line 438. Inter-heater 440 raises the temperature of the first reactor section effluent and returns the heated upper reactor effluent passes to the lower reactor section 414 via line 428. Annular space 442 distributes the heated upper reactor effluent around the lower catalyst bed 418. A lower reactor effluent passes through a center pipe 444 and into annular space 446. A line 448 recovers the lower reactor effluent and passes it to facilities similar to those previously described for recovery of AA product and optional recycle of unconverted bPL, recovery of additives, and removal of by-products.

In this embodiment catalyst is periodically removed from the bottom of reactor vessel 410 by line 443 and replaced at the top of reactor vessel 410 by line 450. Catalyst flows through the vessel by dropping from into line 460 from collection pipes 452 that withdraw catalyst from the annular catalyst bed 418. As catalyst drops from bed 412, transfer pipes 454 add catalyst from catalyst bed 416 and distribute around catalyst bed 418. In turn as catalyst drops from catalyst bed 416, transfer pipes 456 replace it with catalyst withdrawn from heat exchange section 458 of heat exchanger 430 that receives fresh and/or regenerated catalyst from catalyst supply line 450.

The reactor vessel may operate with or without continuous regeneration. In the latter case, deactivated or partially deactivated catalyst withdrawn by line 460 may be discarded or transferred to remote regeneration facilities located on-site or off-site for reactivation and reuse of the spent catalyst. Line 450 will be used to supply reactivated or fresh catalyst to the reactor vessel 410 as catalyst is withdrawn vial line 460.

In those embodiments that use continuous regeneration FIG. 4 shows regeneration system 462 that receives at least partially deactivated catalyst from reaction vessel 420 via line 471 and returns reactivated, and optionally treated catalyst to reactor vessel 410 via lien 450.

In this embodiment the transfer of catalyst to the regeneration system 462 begins with the intermittent passage of catalyst to a lock hopper 464 through line 443 upon the opening and closing of an upper control valve 460. Another control valve 463 regulates the movement of catalyst from lock hopper 464 into a lift vessel 466. When catalyst is ready for regeneration transfer through line 471, control valve 463 is closed and lift gas enters lift vessel 470 via line 468 and is carried to the bottom of lift vessel 466 by lift gas tube 470. The lift gas carries the catalyst upward into a catalyst hopper 472 of regeneration system 462. Lift gas disengages from the catalyst in vessel 472 and is removed from the regeneration section 479 by conduit 475.

Catalyst is regenerated as it flows intermittently from the top to the bottom of regeneration system 462. Intermittent passage of catalyst begins with the opening of a valve 490 in a line 491 that results in catalyst from hopper 472 passing downwardly through a line 473 into an upper chamber 477 of a combustion vessel 476 as catalyst drops into a lower portion 488 of the combustion vessel 476 to replace catalyst the dropped into a lock hopper 492. Valve 491 isolates lock hopper 492 for transfer of catalyst into lift vessel 496. Catalyst is transported from lift vessel 496 into line 450 by closing valve 494 and injecting lift gas into lift vessel 496 via line 447 in the manner 4 previously described.

In various embodiment that regeneration system passes a regeneration gas and may optionally pass one or more treatment and/or purge gases through the regeneration section. A baffle 467 divides the combustion vessel into the upper chamber 477 and the lower chamber 488. The primary regeneration gas enters the regeneration section 462 via a line 478 and passes into the bottom of upper chamber 477, across a bed 482 of deactivation catalyst. A line 474 withdraws the regeneration gas from the top of upper chamber 477. Additional regeneration gas or treatment gas enter the bottom of lower chamber 488 via line 487. An additional gas stream, typically a treatment gas may also enter a lower contact zone 489 via a line 461. A line 479 withdraws gas from lower chamber 488 below baffle 467. Since lower contact zone 489 communicates with combustion vessel 476, conduit 479 also withdraws gas that enter the lower contact zone 489.

Figure 5:
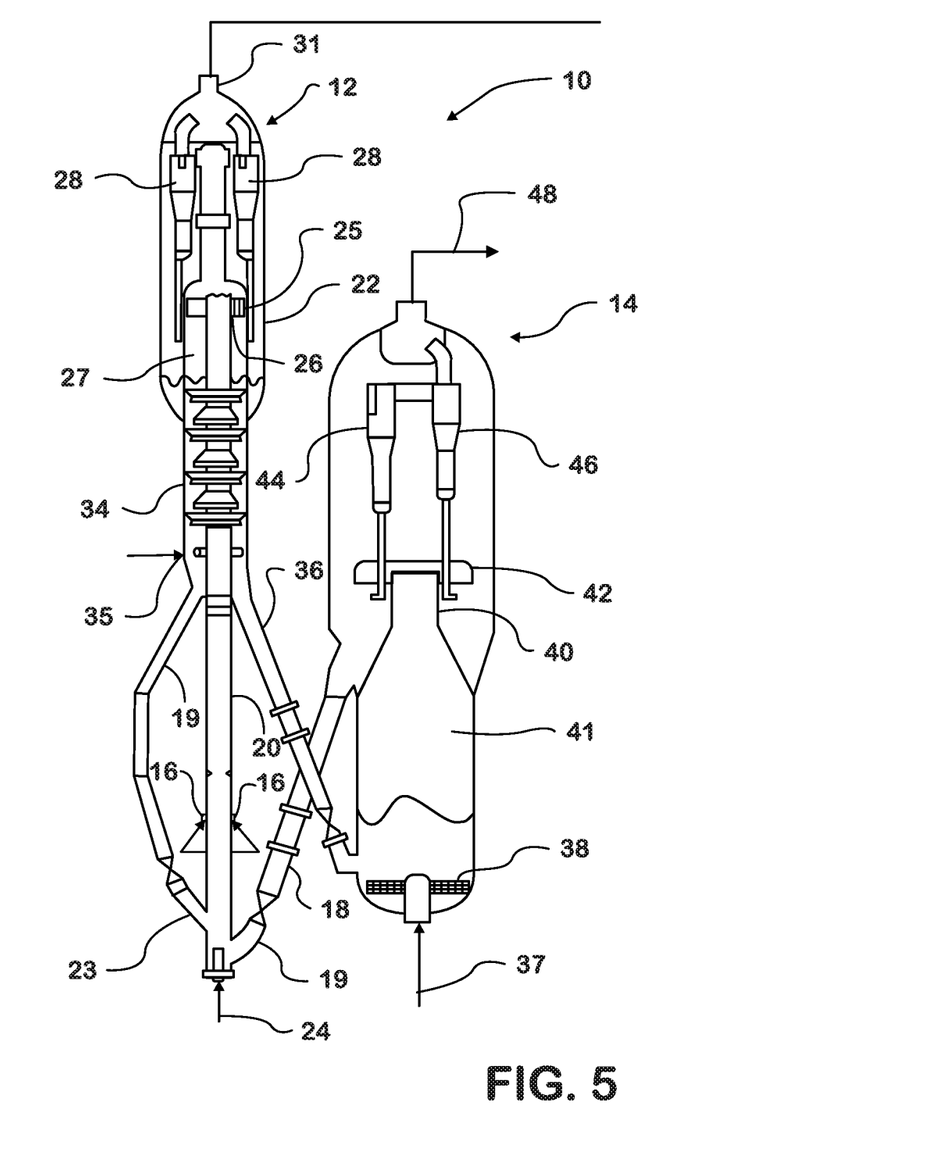
FIG. 5 is a process flow diagram for a fluidized bed operation of the reactor system to produce acrylic acid from bPL according to the methods of this invention.

FIG. 5 presents the method of this invention in an arrangement suitable for commercial practice of the invention in a fluidized reaction configuration. FIG. 5 shows a fluidized reactor arrangement that uses a dilute phase transfer zone as the catalyst contact zone (also referred to as riser.) FIG. 5 shows a typical fluidized reactor arrangement 10 for fluidized catalyst contacting that is integrated with a regeneration zone. In the unit 10 a feed stream is contacted in reactor 12 with a regenerated conversion catalyst of this invention. In an embodiment, regenerated conversion catalyst entering from a regenerator conduit 18 contacts the bPL combined feed stream comprising bPL and one or more of diluents fluidization gases, and other additives as herein described. In most embodiments the regenerated catalyst is at substantially higher temperature than the combined feed and additional heating of the feed by contact with the regenerated catalyst can provide additional fluidization to lift the catalyst and carry up the riser 20 of the reactor 12. The regenerator conduit 18 is in downstream communication with the regenerator 14. The riser 20 has an inlet 19 in downstream communication with said regenerator conduit 18. The regenerator conduit 19 is connected to the riser 20 at a lower end. A control valve located between sections 18 and 19 of the regenerator conduit regulates the flow of catalyst out of the regenerated catalyst conduit and provides a pressure drop that prevents any substantial flow of the feed stream up the section 18 of the regeneration conduit.

In another aspect of the invention spent cracking catalyst entering from a recycle catalyst conduit 19 and a riser inlet tube 23 is contacted with the combined bPL feed stream riser 20 of the reactor 12 without the spent catalyst undergoing regeneration. Again a valve at the top of riser inlet tube 23 regulates the flow of catalyst through tube 23. In this aspect the spent catalyst recycle will allow additional control of the temperature and/or the activity of the catalyst in the reactor 12 and can increase the coke concentration of catalyst in the reactor 12 to aid in the regulation of regenerator temperatures and catalyst regeneration.

The recycle of spent catalyst through the recycle catalyst conduit can also be used to increase the ratio of catalyst-to-feed in the reactor. In one embodiment the catalyst-to-feed weight ratio is in a range between 5 and 20 and preferably between 10 and 15. In some embodiments portions of the bPL feed may be fed to the riser 20 through elevated distributors 16 and this can be used to maintain conversion of the bPL as the catalyst passes up the riser 20.

The recycle conduit 19 is in downstream communication with a riser outlet 25. The recycle conduit 19 is connected to the riser 20 at the outlet end of the recycle conduit by riser tube 23. The recycle conduit 19 bypasses the regenerator 14 by being in downstream communication with the riser outlet 25 and the riser tube 23 being in direct, downstream communication with the recycle conduit. Consequently, spent catalyst entering the recycle conduit 19 passes back to the riser 20 before any of it enters the regenerator 14. The recycle conduit 19 has no direct communication with the regenerator 14.

The AA containing product gases and spent catalyst in the riser 20 are thereafter discharged from the riser outlet 25 into a disengaging chamber 27 which contains the riser outlet. The gas stream containing AA product is disengaged from the catalyst in the disengaging chamber 27 using a rough cut separator 26. Cyclonic separators which may include one or two stages of cyclones 28 in the reactor vessel 22 further separate catalyst from AA products. Product containing gases exit the reactor vessel 22 through an outlet 31 for transport to downstream product separation facilities to recover AA, recycle bPL, diluents and additives. In another embodiment, the recycle conduit 19 and the regenerator conduit 18 are in downstream communication with the disengaging chamber 27. The outlet temperature of the product containing gas leaving the riser 20 should be less than 325° C. and preferably less than less than 300° C.

After separation from product containing gases catalyst falls into a stripping section 34 where an inert gas is injected through a nozzle 35 and distributed to purge any residual product vapor or gas. After the stripping operation, a portion of the spent catalyst is fed to the catalyst regenerator 14 through a spent catalyst conduit 36. The catalyst regenerator 14 may be in downstream communication with the riser 20, specifically, the riser outlet 25. In certain embodiments a portion of the spent catalyst is recycled through recycle catalyst conduit 19 to the riser 20 as previously described.

FIG. 5 depicts a vessel 14 for the regeneration of catalyst having a combustor 41 as the primary zone for the regeneration of the catalyst by combustion of the coke and the displacement of other volatile compounds from the surface of the catalyst. Other embodiments of the invention may use other configurations and arrangement of regenerators. In the catalyst regenerator 14, a stream of oxygen-containing gas, such as air, is introduced from line 37 through a distributor 38 to contact the coked catalyst, burn coke deposited thereon, and provide regenerated catalyst and a gas stream comprising the products of the combustion and generally referred to as flue gas. Catalyst and air flow upwardly together through the combustor 41 and along a combustor riser 40 located within the catalyst regenerator 14. The catalyst which is at least partially regenerated is discharged through a disengager 42 to effect an initial separation of the catalyst from the flue gas. A series of cyclonic separation steps in cyclones 44 and 46 effect further separation of regenerated catalyst and flue gas. The cyclones direct the catalyst separated therein into the conduits that extend downwardly from the cyclones and are referred to as diplegs. The flue gas which is relatively free of catalyst exits cyclones 44, 46 and flows out of the regenerator vessel 14 through line 48. Regenerated catalyst is recycled back to the reactor riser 20 through the regenerated catalyst conduit 18.

The flue gas will typically contain carbon dioxide, water vapor, and lesser amounts of carbon monoxide. Depending on the type and the erosion properties of the catalyst the flue gas may also contain small amounts of extremely fine catalyst particles typically in the range of between 0.2 and 2 micrometers which in some applications will require additional treatment of the flue gas for removal of such particles.

The acrylic acid produced according to the methods described herein may be used for various applications. For example, acrylic acid may be used to make polyacrylic acid for superabsorbent polymers (SAPs). The SAPs find use in diapers, adult incontinence products, and feminine hygiene products among other things.

In some aspects, provided is a method for producing a superabsorbent polymer, by: polymerizing the acrylic acid produced according to any of the methods described herein in the presence of a cross-linker to produce the superabsorbent polymer.

EXAMPLES

The following Examples are merely illustrative and are not meant to limit any aspects of the present disclosure in any way.

Example 1—Conversion of bPL to Acrylic Acid Using a Zeolite

This Example demonstrates the production of acrylic acid from bPL using a zeolite.

A mixture of bPL (3.0 g) and phenothiazine (9.0 mg) was added using a needle value to a mixture of sulfolane (40.0 g) and Zeolite Y hydrogen (20.0 g) at 165° C. with 50 psi of carbon monoxide. Zeolite Y hydrogen (80:1 mole ratio $SiO_2/Al_2O_3$, powder S.A. 780 $m^2/g$) was dried under vacuum at 100° C. for one day before use. Phenothiazine was the polymerization inhibitor used. Sulfolane was the solvent used, and was dried over 3 Å molecular sieves prior to use. The bPL was added slowly using the needle valve over about 8.6 minutes. The reaction mixture was heated to 170° C. to produce acrylic acid.

The reaction was monitored by infrared spectroscopy (IR). The reaction was observed to be completed after about 3 hours, when no bPL was detectable by IR.

The zeolite was then filtered off from the reaction mixture, and a sample of the resulting mixture was dissolved in deuterium ($D_2O$) and chloroform ($CDCl_3$) for nuclear magnetic resonance (NMR) analysis. The observed vinyl peaks between δ 5.80 and 6.47 ppm in the $^1H$ NMR confirmed the production of acrylic acid.

Example 2—Vapor Phase Conversion of bPL to Acrylic Acid Using a H-ZSM5

Vapor phase conversion of β-propiolactone to acrylic acid was performed in packed-bed reactor using H-ZSM-5 (ACS Materials LLC, Si:Al=38, diameter 2 mm, surface area >=250 $m^2/g$) as a catalyst. 11 grams of H-ZSM-5 catalyst were loaded into jacketed stainless steel 316 pipe reactor (ID 0.5 inch), the catalyst was supported between glass beads columns (stainless steel wool was placed below and above glass beads). Multi point thermocouple was inserted through the center of the reactor and hot oil was circulated through the reactor jacket to maintain the desired reactor temperature. bPL was fed to the reactor by means of saturator: $N_2$ at the rate of 28 g/hr was flown into the bottom of the vessel containing liquid bPL at a=94° C., this resulted in bPL feed rate of 5 g/hr. The pressure of reactor and saturator was maintained at 9.5 psig. The reaction products were absorbed in chilled to 10° C. dichloromethane and the solution of reaction products in dichloromethane was analyzed by gas chromatography. The line between the saturator and the reactor as well as the line between the reactor and absorber were heat traced to prevent condensation of bPL and acrylic acid. The reaction was conducted at the reactor temperature of 210° C. At this conditions bPL conversion of greater than 99.9% was observed with selectivity of acrylic acid product of greater than 98% (WHSV at these conditions was 0.45 $h^{-1}$).

What is claimed is:

1. A method of producing acrylic acid from a β-propiolactone, the method comprising:
   contacting the β-propiolactone with a heterogeneous catalyst comprising crystalline microporous solid under vapor phase conditions, wherein the crystalline microporous solid comprises zeolite in cation exchanged form;
   maintaining the β-propiolactone in the vapor phase; and
   converting the β-propiolactone into acrylic acid.

2. The method of claim 1, wherein the zeolite has a framework type of MFI pentasil, FAU faujasite, MALI mordenite, BEA (beta) or MWW zeolite structures and a one-dimensional crystalline configuration, two-dimensional crystalline configuration, or three-dimensional crystalline configuration.

3. The method of claim 1, wherein the zeolite in cation exchanged form is zeolite ion exchanged with one or more cations selected from the group consisting of $Na^+$, $K^+$, $Ca^{2+}$, $Mg^{2+}$, $cu^{2+}$, and $Cu^+$.

4. The method of claim 1, wherein the β-propiolactone is provided at a WHSV of between 0.1 $h^{-1}$ to 2.1 $h^{-1}$.

5. The method of claim 2, wherein the β-propiolactone is provided at a WHSV of from 0.3 $h^{-1}$ to 0.9 $h^{-1}$.

6. The method of claim 1, wherein the acrylic acid produced is continuously isolated.

7. The method of claim 1, wherein the acrylic acid is produced at a yield of at least 50%.

8. The method of claim 1, wherein the acrylic acid is produced at a temperature of between 100° C. and 300° C.

9. The method of claim 1, wherein the β-propiolactone and the catalyst are further combined with a solvent.

10. The method of claim 9, wherein the solvent comprises a polar aprotic solvent.

11. The method of claim 9, wherein the solvent comprises sulfolane.

12. The method of claim 1, wherein the acrylic acid produced has a purity of greater than 95%.

13. The method of claim 1, wherein the contacting comprises: passing a vapor phase feed stream comprising the β-propiolactone to a fixed bed of the heterogeneous catalyst at conversion conditions; recovering a product stream comprising acrylic acid from the fixed bed; and separating acrylic acid from the product stream in a separation zone.

14. The method of claim 13, wherein the conversion conditions comprise a pressure in a range of 200 to 20 mm Hg.

15. The method of claim 13, wherein the vapor feed stream comprises a polymerization inhibitor.

16. The method of claim 1, wherein the contacting comprises:
   passing a vapor phase feed stream comprising the β-propiolactone to a moving bed of the heterogeneous catalyst at conversion conditions;
   recovering a product stream comprising acrylic acid from the moving bed;
   separating acrylic acid from the product stream in a separation zone; and,
   periodically withdrawing partially deactivated catalyst from the moving bed and replacing the deactivated catalyst with fresh catalyst having a greater activity for conversion of β-propiolactone to acrylic acid than the partially deactivated catalyst withdrawn from the moving bed.

17. The method of claim 16, wherein the fresh catalyst entering the moving bed is heated before contacting the vapor phase feed stream.

18. The method of claim 16, wherein the deactivated catalyst passes to a regeneration zone where the deactivated catalyst is contacted with a regeneration gas to partially restore its activity and produce regenerated catalyst, and a portion of the regenerated catalyst is returned to the moving bed as the fresh catalyst.

19. The method of claim 1, wherein the contacting comprises:
   passing a vapor phase feed stream comprising the β-propiolactone into contact with the heterogeneous catalyst in a fluidized reaction zone;
   maintaining the heterogeneous catalyst under fluidized conditions;
   disengaging a vapor phase product stream from the fluidized catalyst; and
   recovering an acrylic acid product stream from the vapor phase product stream.

20. The method of claim 16, wherein the vapor phase product stream undergoes separation in at least one cyclone separator.

21. The method of claim 16, wherein the heterogeneous catalyst is maintained as a fluidized bed and the vapor phase feed stream is injected into the fluidized bed having a catalyst density of at least 25 lbs per cubic foot and the vapor phase product stream is recovered from the fluidized bed.

22. The method of claim 16, wherein the vapor phase feed stream contacts the fluidized catalyst in a dilute phase transfer mode wherein the dilute phase has a catalyst density of less than 20 lbs per cubic foot; a transport gas carries the catalyst particles through a dilute phase transfer zone and the catalyst is disengaged from the transport gas at the end of the dilute phase transfer zone to recover the vapor phase product stream.

23. The method of claim 16, wherein contact of the heterogeneous catalyst with the β-propiolactone produces spent catalyst that contains carbon deposits; a portion of the spent catalyst particles enter a regeneration zone wherein a regeneration gas contacts the catalyst to remove the carbon deposits from the spent catalyst and produce a regenerated catalyst; and the regenerated catalyst is returned to the moving bed.

24. The method of claim 16, further comprising isolating the acrylic acid.

25. The method of claim 24, wherein the acrylic acid is isolated by distillation.

26. The method of claim 1, wherein the β-propiolactone is produced from ethylene oxide and carbon monoxide.

27. A method of producing a superabsorbent polymer, comprising:
   polymerizing acrylic acid produced according to the method of claim 1 in the presence of a cross-linker to produce the superabsorbent polymer.

28. The method of claim 1, wherein the β-propiolactone and the heterogeneous catalyst are contacted in the presence of a polymerization inhibitor.

29. The method of claim 28, wherein the polymerization inhibitor comprises phenothiazine.

30. The method of claim 1, wherein the heterogeneous catalyst has both weakly acidic and weakly basic sites.

31. The method of claim 1, wherein the heterogeneous catalyst has a balance between surface acidity and basicity.

32. The method of claim 1, wherein the zeolite in cation exchanged form has a $SiO_2/Al_2O_3$ ratio in a range of between 1.1 to 120.

33. The method of claim 1, wherein the zeolite in cation exchanged form has a fractional exchange degree of $K^+$ that is higher than 70%.

34. The method of claim 1, wherein the zeolite in cation exchanged form has a micropore volume of at least 30%.

35. The method of claim 1, wherein the zeolite in cation exchanged form has a particle size between 0.1 μm and 1.8 μm.

36. The method of claim 1, wherein the zeolite in cation exchanged form having a micropore volume between 30% and 45%.

* * * * *